(12) United States Patent
Berndtsson

(10) Patent No.: US 6,284,548 B1
(45) Date of Patent: Sep. 4, 2001

(54) BLOOD TESTING METHOD AND APPARATUS

(75) Inventor: Ingemar Berndtsson, Sollentuna (SE)

(73) Assignee: Boule Medical AB, Stockholm (SE)

( * ) Notice: Subject to any disclaimer, the term of this patent is extended or adjusted under 35 U.S.C. 154(b) by 0 days.

(21) Appl. No.: 09/239,804

(22) Filed: Jan. 29, 1999

(30) Foreign Application Priority Data

Feb. 6, 1998 (SE) .................................................. 9800214

(51) Int. Cl.$^7$ ...................................................... B01L 1/00
(52) U.S. Cl. .......................... 436/179; 422/81; 422/100; 422/103; 436/52; 436/180
(58) Field of Search ............................ 422/81, 100, 103; 436/52, 179, 180

(56) References Cited

U.S. PATENT DOCUMENTS

| | | | |
|---|---|---|---|
| 3,419,358 | * 12/1968 | Smythe et al. | 436/179 |
| 3,649,218 | * 3/1972 | Pontigny | 137/13 |
| 3,811,326 | * 5/1974 | Sokol . | |
| 3,831,618 | * 8/1974 | Liston | 137/154 |
| 4,097,921 | * 6/1978 | Raffaele | 364/416 |
| 4,868,129 | * 9/1989 | Gibbons et al. | 436/179 |
| 5,077,017 | * 12/1991 | Gorin et al. | 422/100 |
| 5,089,234 | * 2/1992 | Preston | 422/103 |
| 5,284,773 | * 2/1994 | Kulkarni et al. | 436/52 |
| 5,512,248 | * 4/1996 | Van | 422/100 |
| 5,599,718 | * 2/1997 | Gorog | 436/69 |
| 5,976,465 | * 11/1999 | Luzzana et al. | 422/82.03 |
| 6,067,842 | * 5/2000 | Gygax et al. | 73/23.34 |

* cited by examiner

*Primary Examiner*—John Kim

(57) ABSTRACT

A method for performing a dilution step in a blood testing apparatus of a small, defined volume of a blood sample contained in a capillary tube, comprises the steps of providing an adapter for receiving the capillary tube, connecting the adapter to a conduit for diluting liquid, directing a flow of diluting liquid through the conduit and the adapter and at least partly through the capillary tube received therein, and collecting the defined volume of blood sample and the diluting liquid in a vessel. In a blood testing apparatus adapted for performing dilution of a small defined volume of a blood sample contained in a capillary tube, an adapter is inserted in a diluting liquid conduit of the apparatus. The adapter is arranged to receive the capillary tube such that flow of the diluting liquid through the conduit passes at least partly through the capillary tube.

9 Claims, 4 Drawing Sheets

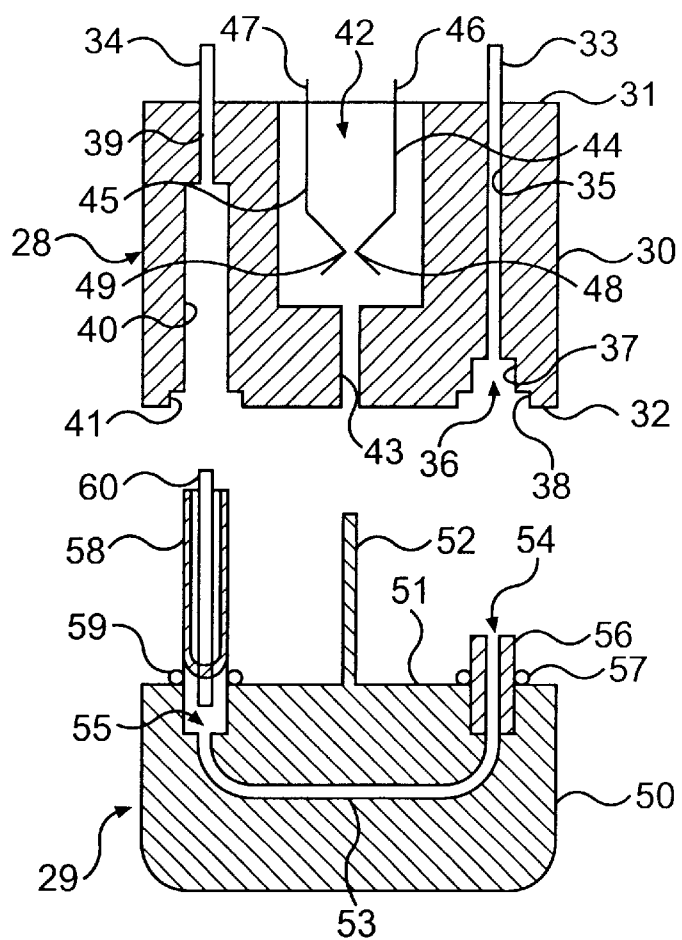
FIG. 4a
FIG. 4b
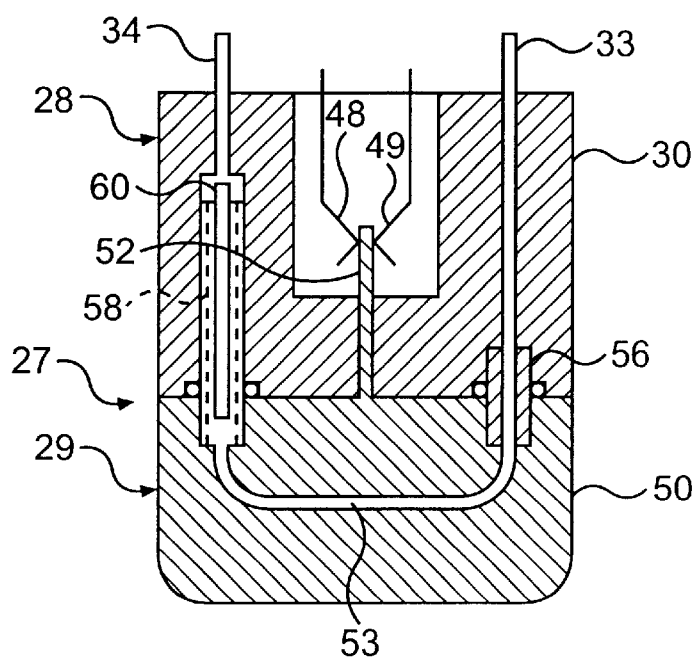
FIG. 5

BLOOD TESTING METHOD AND APPARATUS

FIELD OF THE INVENTION

The present invention concerns a blood testing method, and more particularly a method for performing a dilution step in a blood testing apparatus. The invention also concerns a blood testing apparatus adapted for performing dilution of a blood sample.

BACKGROUND OF THE INVENTION

When using a blood testing apparatus, a blood sample is normally taken by venipuncture. The blood is introduced into a small tube containing, for instance, 5 ml. From this tube, blood is sucked into a charging tube of the apparatus. Suction is stopped when the blood reaches a detector indicating that a sufficient amount of blood has been introduced into the apparatus. A well-defined volume of the blood sample, typically 25 μl, is flushed by a defined volume, typically 5 ml, of a diluting liquid into a mixing vessel, where the sample is pre-diluted to typically 1:200. The diluted sample is further diluted 1:200 to a dilution ratio of 1:40000 for counting red blood cells and 1:1 to a dilution ratio of 1:400 for counting white blood cells.

When, however, a sample is taken from a finger tip, which is often practised when children are involved, the blood volume is small and is not sufficient for sucking into the apparatus for dilution as described above. Instead, a manual dilution procedure is practiced. The blood sample is manually collected in a small vessel and a defined volume thereof, typically 25 μl, is introduced into a small diameter glass tube, i.e., a capillary tube often referred to as a "microcap", or a "mini" or "micro" pipette, which sucks the sample by capillary action. The volume contained in the capillary tube is pre-diluted 1:200 by means of a separate dispenser. This pre-diluted sample is then sucked into the apparatus, whereupon final dilution takes place as when a venipuncture test is performed. However, this procedure is circumstantial in that it requires an extra manual step.

It would be desirable, thus, to simplify the procedure when making blood tests by way of finger tip puncture, and it is the object of the present invention to provide a method and a device that enable this.

SUMMARY OF THE INVENTION

According to the present invention, the blood sample is initially introduced, as before, in a capillary tube. The capillary tube is placed in an adapter, which is placed in a conduit from a source of diluting liquid to a mixing vessel where the sample is directly pre-diluted, typically 1:200. The manual pre-dilution step is, thus, superfluous. The capillary tube may remain within the adapter until another capillary tube having a new sample is inserted, since the used capillary tube may be regarded as just an empty glass tube.

More specifically, the method of the present invention for performing a diluting step in a blood testing apparatus of a small, defined volume of a blood sample contained in a capillary tube comprises the steps of providing an adapter for receiving the capillary tube; connecting the adapter to a conduit for diluting liquid; directing a flow of diluting liquid through the conduit and the adapter and at least partly through the capillary tube received therein; and collecting the defined volume of blood sample and the diluting liquid in a vessel.

In a blood testing apparatus according to the present invention adapted for diluting a small defined volume of a blood sample contained in a capillary tube, the apparatus including a diluting liquid conduit, an adapter is inserted in the diluting liquid conduit, the adapter being arranged to receive the capillary tube such that flow of diluting liquid through the diluting liquid conduit passes at least partly through the capillary tube.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Embodiments of the present invention will now be described, reference being made to the accompanying drawings, wherein:

FIGS. 4a and b is a schematic cross section through an adapter in an disassembled state; and FIG. 5 is a corresponding section through the adapter of FIG. 4 in an assembled, operative state.

DETAILED DESCRIPTION

Figure 1:
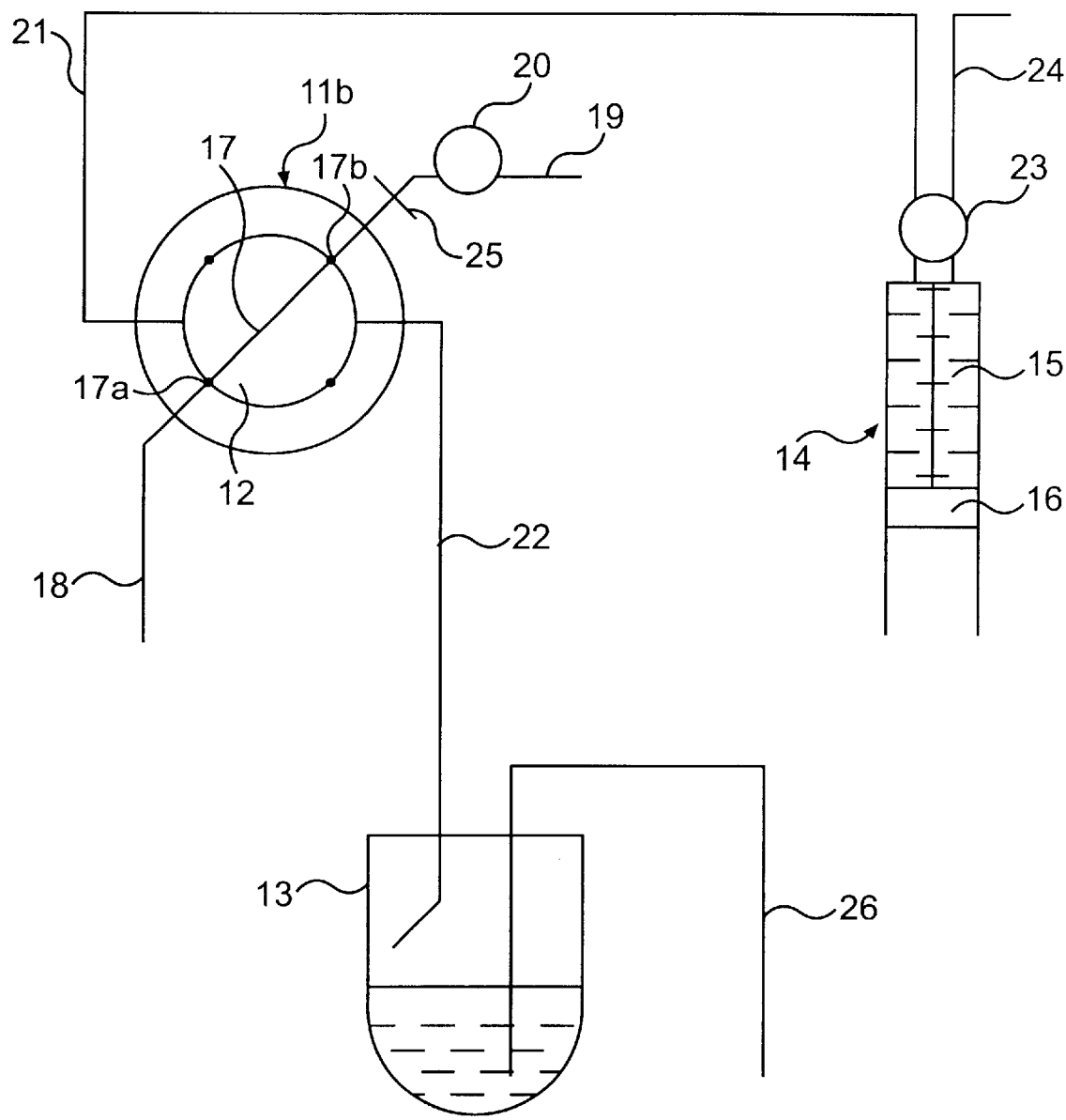
FIG. 1 is a schematic cross section through a prior art blood testing apparatus.

For facilitated understanding of the present invention, reference is made first to the typical prior art arrangement shown in FIG. 1, wherein 11 is a turning valve having a rotatable valve body 12, 13 is a mixing vessel and 14 a syringe including a cylinder 15 and a piston 16 axially movable within the cylinder.

The rotatable valve body 12 has a through channel 17 and is positionable in at least two different positions. In a first position (shown in FIG. 1), a first end of the through channel 17 communicates with a conduit 18, which is a suction or charging conduit, and a second end of the through channel communicates with a conduit 19 having a valve 20 therein and leading to a non-shown suction device, such as a syringe. In a second position of the valve body 12, the first end 17a of the through channel 17 communicates with a conduit 21 leading to the syringe 14, and the second end 17b communicates with a conduit 22 leading to the mixing vessel 13. The syringe 14 has in its end a valve 23, which selectively may put the cylinder 15 in communication with the conduit 21 and a conduit 24 leading to a non-shown source of diluting liquid.

The function of the prior art device when making a venipuncture blood test is as follows: The valve body 12 is positioned in the position shown in FIG. 1, and a blood sample is caused to be sucked into the conduit 18, the through channel 17 and the conduit 19 by means of the non-shown sucking device. As soon as the sample reaches a detector 25 located in the conduit 19, the valve 20 is shut and the suction stopped. Now, the through channel contains an accurately defined volume of blood sample, typically 25 µl. Upon rotation of the valve body 12 so as to place its ends, and, consequently, the defined volume of blood sample in connection with the conduits 21 and 22, the piston 16 is displaced so as to in turn displace a defined volume (typically 5 ml) of diluting liquid contained within the cylinder 15 through the conduit 21, the through channel 17 and the conduit 22 into the mixing vessel 13, thereby bringing along the defined volume of blood sample contained within the through channel 17 to be mixed with and diluted by the diluting liquid in the mixing vessel.

As initially discussed, when taking a fingertip blood sample, the volume is not sufficient to be sucked into the through channel 17. Instead, a manual pre-dilution takes place outside the apparatus, and the pre-diluted sample is introduced into the mixing vessel 13 through a conduit 26, and then this sample is further diluted by the volume of diluting liquid contained in the cylinder 15.

In order to avoid the manual dilution step, which is time consuming and may cause contamination of the sample as well as involve a risk of transmission of infection, the present invention proposes insertion of an adapter into a flow path of diluting liquid, said adapter including means for receiving a capillary tube or the like blood sample collector.

Figure 2:
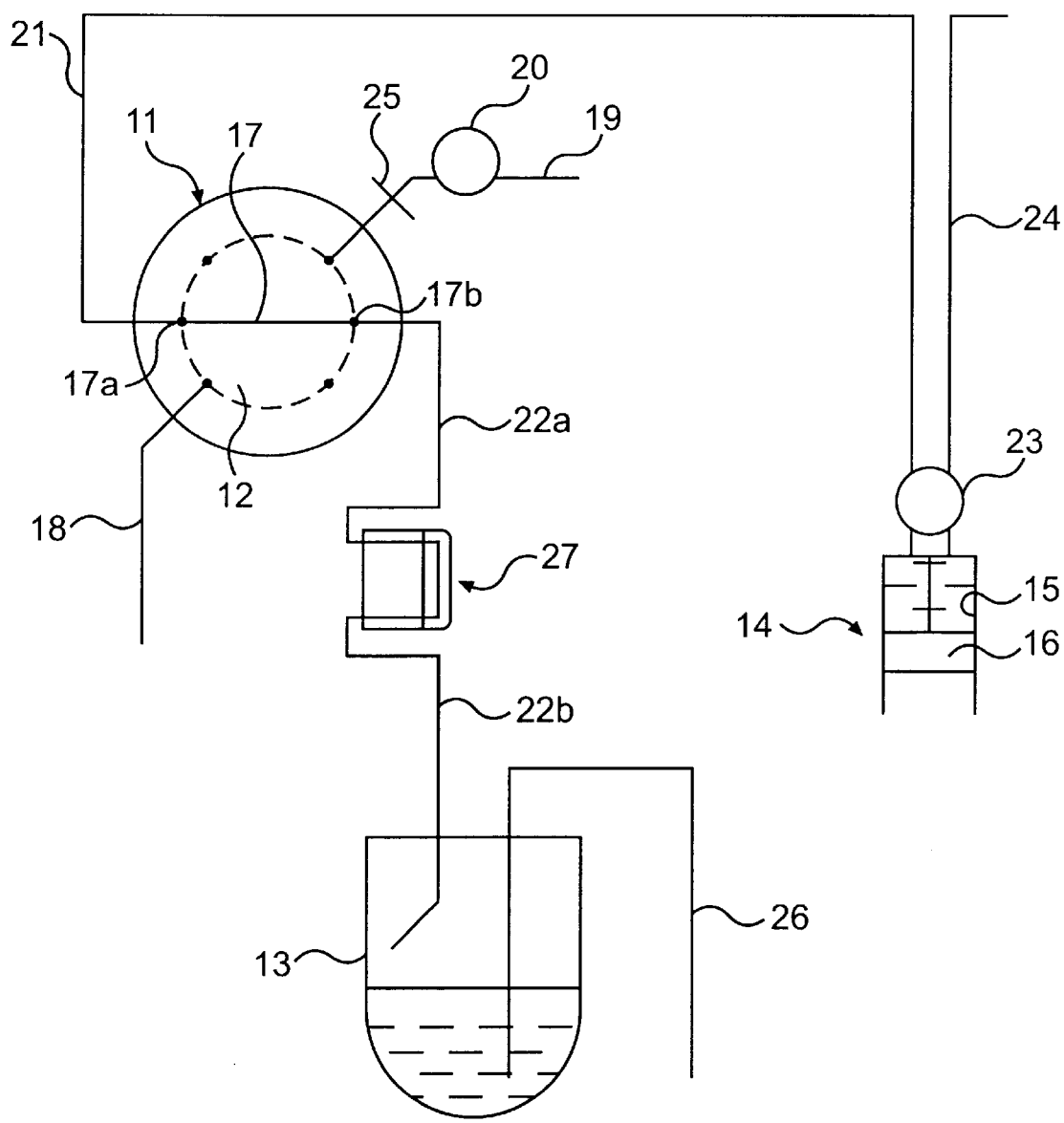
FIG. 2 is a corresponding representation of an improved blood testing apparatus according to the present invention having an adapter inserted in a conduit of the apparatus.
Figure 3:
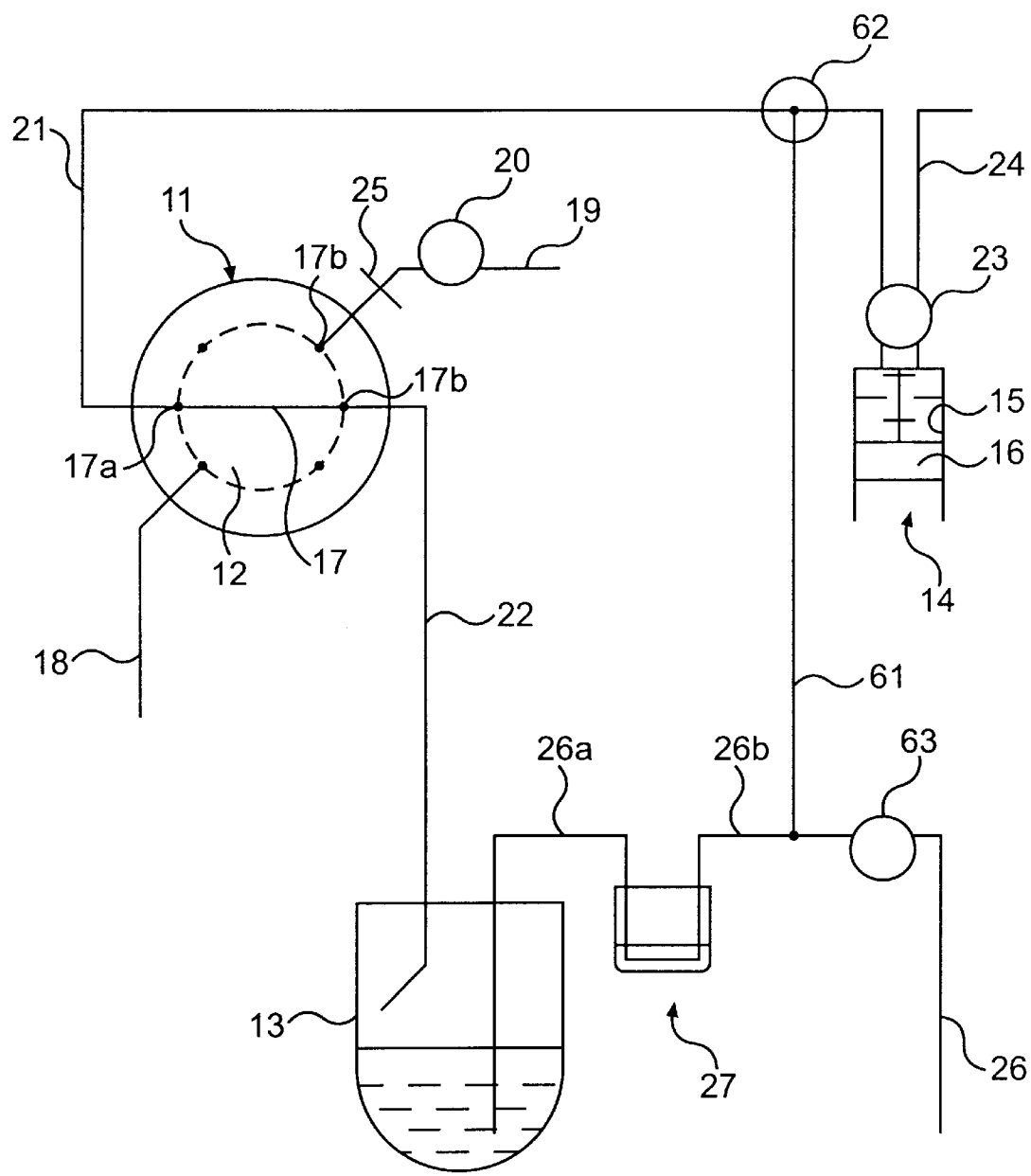
FIG. 3 is a representation corresponding to that of FIG. 2, but showing an adapter inserted in a conduit of the apparatus at a more preferred location.

FIG. 2 shows one location of an adapter 27 between portions 22a, 22b of the conduit 22, and FIG. 3 shows another preferred location thereof between portions 26a, 26b of the conduit 26.

FIG. 4 shows an embodiment of an adapter according to the present invention in a disassembled state. The adapter 27 includes a stationary part 28 and a movable part 29.

The stationary part comprises a block-shaped body 30 having opposite faces 31 and 32, at least the face 32 preferably being flat. Inlet means and outlet means adapted to be connected to the conduit 26 (FIG. 2) or the conduit 22 (FIG. 3), e.g. in the shape of pipe sockets 33, 34, respectively, are arranged at the face 31.

The inlet socket 33 communicates with a bore 35 extending through the body 30 to open at its face 32. Coaxially to the bore 35 a stepped recess 36 is formed in the face 32. The recess has a relatively narrow and deep portion 37 and a relatively wide and shallow portion 38.

Also the outlet socket 34 communicates with a bore 39 extending through the body 30 to open at its face 32. Starting from the face 32, the bore 39 has a deep widened portion 40 and a relatively shallow, further widened portion 41.

Centrally between the bores 35 and 39 there is provided in the face 31 a relatively wide aperture 42. A bore 43 extends from the bottom of the aperture 42 to open centrally in the face 32. Centrally in the aperture 42 are mounted two contact tongues 44, 45 having terminal ends 46, 47, respectively, projecting outside the face 31 and spaced contact edges 48, 49, respectively, located in the bottom region of the aperture 42 at substantially equal distances from the axis of the bore 43. The axes of the bores 35, 43 and 39 are parallel, perpendicular to the face 32 and located in a common plane.

The movable part 29 of the adapter is likewise constituted by a block-shaped body 50 having a flat face 51. A central pin 52 extends perpendicularly from the face 51. It has a diameter corresponding to that of the bore 43 and a length somewhat exceeding the distance between the face 32 and the contact edges 48, 49. At least an outer portion of the pin 52 is electrically conductive.

Within the block 50 there is provided an internal channel 53 having mouths 54, 55 in the face 51 at locations spaced from the pin 52 distances corresponding to the spacings between on one hand the bore 33 and the bore 43, and on the other hand the bore 39 and the bore 43. The axis of the pin 52 and the axes of the mouths 54 and 55 are parallel, perpendicular to the face 51 and located in a common plane.

In the region of the mouth 54 the channel 53 has a widened portion in which is inserted a connection tube 56 having a diameter corresponding to that of the portion 37 of the recess 36 and an extension outside the face 51 corresponding to the depth of the recess 36. A sealing ring 57 having an outer diameter corresponding to that of the wider portion 38 of the recess 36 is arranged around the tube 56.

Correspondingly, in the region of the mouth 55 the channel 53 has a widened portion in which is inserted a relatively long connection tube 58 having a diameter corresponding to that of the portion 40 of the recess 36 and an extension outside the face 51 somewhat less than the depth of the deep recess portion 40. A sealing ring 59 having an outer diameter corresponding to that of the portion 41 of the bore 39 is arranged around the tube 58.

The connection tube 58 is adapted to internally receive a capillary tube 60 having open ends, thereby to serve also as a protective sheathing for the capillary tube. According to the present invention, it be preferred that the inner diameter of the connection tube is larger than the outer diameter of the capillary tube as shown by the part section of the wall of the connection tube in FIG. 4. The capillary tube is introduced into the connection tube either from the free end thereof or through a longitudinal slot in the side wall thereof substantially corresponding to the section shown in FIG. 4. The capillary tube is in no way kept centrally within the connection tube, but is allowed to move freely within the confines of its inner wall. Lengthwise, the capillary tube is kept against movement towards the internal channel 53 by any suitable abutment means or by the cross section of this channel being smaller than the cross section of the capillary tube.

After a capillary tube charged with a blood sample has been introduced into the connection tube 58, the moveable adapter part 29 is assembled with the stationary part 28 by inserting the connecting tube 58 with the capillary tube 60 into the bore portion 40, the pin 52 into the bore 43 and the connection tube 56 into the portion 37 of the bore 35, such that the sealing rings 57, 59 seal against the respective recess portion 38, 41. In this position, shown in FIG. 5, lengthwise movement of the capillary tube towards, or into, the bore 39 is restricted by any suitable abutment means or by the cross section of the bore 39 being smaller than the cross section of the capillary tube. The adapter is now prepared for a dilution step, in which a diluting liquid is introduced through the inlet pipe socket 33 and further guided through the bore 35, the connection tube 56 and the channel 53 to the connection tube 58. There, the diluting liquid is free to flow around the capillary tube as well as through it, thereby displacing the blood sample contained therein out off the capillary tube to mix with the diluting liquid in the mixing vessel 13.

The dilution step is advantageously initiated by an electrically conductive forward end of the pin 52 contacting both contact edges 48, 49 of the contact tongues 44, 45 whose terminal ends 46, 47 are connected by suitable wiring to control means of the blood testing apparatus (not shown).

In the embodiment of FIG. 2, to perform a pre-dilution step, a first volume of diluting liquid is forced by the piston 16 through the conduit 21, the through channel 17 and the conduit part 22a, through the adapter 27 and the conduit part 22b into the mixing vessel 13. Thereafter, the valve 23 is shifted so as to allow re-charging the syringe with a further volume of diluting liquid.

In the preferred embodiment of FIG. 3, where the adapter 27 is inserted in the conduit 26 between two parts 26a, 26b thereof, on end of a diluting liquid conduit 61 is connected to the conduit 26b, whereas its other end is connected to a T-valve 62 in the conduit 21. There is also a valve 63 separating the open end of the conduit 26 (which is used for introduction of a manually diluted blood sample) from the conduit part 26b. In the pre-dilution step, the diluting liquid is forced by the piston 16 through the valve 62 into the conduit 61, through the conduit part 26b, the adapter 27 and the capillary tube into the mixing vessel 13. The final diluting step is then performed with the valve body 12 in the position shown in FIG. 3 and the valve 62 shifted so as to direct diluting liquid from the syringe 14 through the conduit 21, the through channel 17 and the channel 22 into the mixing vessel 13 to mix there with the pre-diluted blood sample.

Due to the difference in cross sections of the connection tube 58 (inner diameter) and the capillary tube 60 (outer diameter), there is no need to remove the capillary tube after a dilution step has been performed (unless a further capillary tube dilution is to be performed), since there is sufficient cross section left to allow flow in any direction past the capillary tube.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for performing a dilution step in a blood testing apparatus of a small, defined volume of a blood sample contained in a separate capillary tube having open ends, comprising the steps of:

providing an adapter for removably receiving the capillary tube;

placing a capillary tube in the adapter;

inserting the adapter between a relatively upstream portion and a relatively downstream portion of a conduit for diluting liquid;

directing a flow of diluting liquid through the conduit and the adapter and at least partly through the capillary tube received therein; and collecting the defined volume of blood sample and the diluting liquid in a vessel.

2. A blood testing apparatus adapted for performing dilution of a small defined volume of a blood sample contained in a separate capillary tube having open ends, said apparatus including a diluting liquid conduit and an adapter insertable in said diluting liquid conduit between a relatively upstream portion and a relatively downstream portion thereof, said adapter being arranged to receive said capillary tube such that flow of diluting liquid through said diluting liquid conduit passes at least partly from said relatively upstream portion through said capillary tube to said relatively downstream portion, wherein said adapter includes a stationary part provided with first and second connecting means for connection to said diluting liquid conduit, and a moveable part provided with receiving means for said capillary tube and being attachable to said stationary part in a position enabling flow of diluting liquid at least partly through said capillary tube.

3. An apparatus as claimed in claim 2, wherein said diluting liquid conduit is a conduit leading from a source of diluting liquid to a mixing vessel.

4. An apparatus as claimed in claim 2, wherein:

said stationary part includes first and second channel means communicating with said first and second connecting means, respectively;

said moveable part includes third and fourth connecting means and third channel means therebetween; and said third and fourth connecting means are adapted to be connected to said first and second channel means, respectively, when said moveable part is attached to said stationary part.

5. An apparatus as claimed in claim 4, wherein one of said third and fourth connecting means provides said receiving means for said capillary tube.

6. An apparatus as claimed in claim 5, wherein said one of said third and fourth connecting means is an outlet connecting means of said movable part.

7. An apparatus as claimed in claim 5, wherein said receiving means is a tubular body having an internal cross section exceeding the external cross section of said capillary tube.

8. An apparatus as claimed in claim 4, wherein said receiving means is a tubular body having an internal cross section exceeding the external cross section of said capillary tube.

9. An apparatus as claimed in claim 2, including actuating means for initiating flow of diluting liquid from said source of diluting liquid through said diluting liquid conduit, said actuating means responding to said moveable part being attached to said stationary part.

* * * * *